United States Patent
Lamego

(10) Patent No.: US 9,723,997 B1
(45) Date of Patent: Aug. 8, 2017

(54) ELECTRONIC DEVICE THAT COMPUTES HEALTH DATA

(71) Applicant: Apple Inc., Cupertino, CA (US)

(72) Inventor: Marcelo M. Lamego, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 44 days.

(21) Appl. No.: 14/617,422

(22) Filed: Feb. 9, 2015

Related U.S. Application Data

(60) Provisional application No. 62/056,299, filed on Sep. 26, 2014.

(51) Int. Cl.
| | |
|---|---|
| *A61B 5/0205* | (2006.01) |
| *A61B 5/1455* | (2006.01) |
| *A61B 5/0402* | (2006.01) |
| *A61B 5/00* | (2006.01) |
| *A61B 5/021* | (2006.01) |

(Continued)

(52) U.S. Cl.
CPC .......... *A61B 5/0205* (2013.01); *A61B 5/0402* (2013.01); *A61B 5/14551* (2013.01); *A61B 5/6898* (2013.01); *A61B 5/70* (2013.01); *A61B 5/7203* (2013.01); *A61B 5/742* (2013.01); *A61B 5/7405* (2013.01); *A61B 5/7455* (2013.01); *A61B 5/021* (2013.01); *A61B 5/0261* (2013.01); *A61B 5/02416* (2013.01); *A61B 5/0537* (2013.01)

(58) Field of Classification Search
CPC . A61B 5/0205; A61B 5/0402; A61B 5/14551; A61B 5/6898
See application file for complete search history.

(56) References Cited

U.S. PATENT DOCUMENTS

| | | | |
|---|---|---|---|
| 7,486,386 B1 * | 2/2009 | Holcombe | ............... G01C 3/08 356/4.01 |
| 7,915,601 B2 | 3/2011 | Setlak et al. | |

(Continued)

FOREIGN PATENT DOCUMENTS

| | | |
|---|---|---|
| JP | 2001145607 | 5/2001 |
| WO | WO 2015/030712 | 3/2015 |

OTHER PUBLICATIONS

Ohgi et al., "Stroke phase discrimination in breaststroke swimming using a tri-axial acceleration sensor device," *Sports Engineering*, vol. 6, No. 2, Jun. 1, 2003, pp. 113-123.

(Continued)

*Primary Examiner* — Paula J Stice
(74) *Attorney, Agent, or Firm* — Brownstein Hyatt Farber Schreck, LLP

(57) ABSTRACT

An electronic device includes a camera, an ambient light sensor, and a proximity sensor. The electronic device uses one or more of the camera and the proximity sensor to emit light into a body part of a user touching a surface of the electronic device and one or more of the camera, the ambient light sensor, and the proximity sensor to receive at least part of the emitted light reflected by the body part of the user. The electronic device computes health data of the user based upon sensor data regarding the received light. In some implementations, the electronic device may also include one or more electrical contacts that contact one or more body parts of the user. In such implementations, the health data may be further computed based on the an electrical measurement obtained using the electrical contacts.

21 Claims, 7 Drawing Sheets

(51) Int. Cl.
*A61B 5/024* (2006.01)
*A61B 5/026* (2006.01)
*A61B 5/053* (2006.01)

(56) References Cited

U.S. PATENT DOCUMENTS

| | | | |
|---|---|---|---|
| 2008/0167834 A1* | 7/2008 | Herz | G06F 1/3203 |
| | | | 702/150 |
| 2011/0015496 A1 | 1/2011 | Sherman et al. | |
| 2013/0072145 A1 | 3/2013 | Dantu | |
| 2013/0215042 A1* | 8/2013 | Messerschmidt | G06F 3/041 |
| | | | 345/173 |
| 2013/0310656 A1* | 11/2013 | Lim | A61B 5/6898 |
| | | | 600/301 |
| 2014/0160314 A1* | 6/2014 | Schatvet | H04N 7/142 |
| | | | 348/223.1 |
| 2014/0275832 A1* | 9/2014 | Muehlsteff | A61B 5/0205 |
| | | | 600/301 |

OTHER PUBLICATIONS

Zijlstra et al., "Assessment of spatio-temporal gait parameters from trunk accelerations during human walking," *Gait & Posture,* vol. 18, No. 2, Oct. 1, 2003, pp. 1-10.

* cited by examiner

ELECTRONIC DEVICE THAT COMPUTES HEALTH DATA

CROSS-REFERENCE TO RELATED APPLICATION

This application claims the benefit under 35 U.S.C. §119(e) of U.S. Provisional Patent Application No. 62/056,299, filed on Sep. 26, 2014, and entitled "Electronic Device that Computes Health Data," which is incorporated by reference as if fully disclosed herein.

TECHNICAL FIELD

This disclosure relates generally to health data, and more specifically to an electronic device that computes health data

BACKGROUND

It may be beneficial for a user to have information about his or her health data, including fitness data and wellness data. For example, health data may indicate emergency conditions or to enable the user to maximize fitness or wellness activities. Traditionally, health data is provided to users by health care professionals. However, it may be beneficial for users to have more access to health data.

SUMMARY

The present disclosure discloses systems, apparatuses, and methods related to an electric device that computes health data. An electronic device may include a camera, an ambient light sensor, and a proximity sensor. The electronic device may use one or more of the camera and the proximity sensor to emit light into a body part of a user touching a surface of the electronic device and one or more of the camera, the ambient light sensor, and the proximity sensor to receive at least part of the emitted light reflected by the body part of the user. The electronic device may compute health data of the user based upon sensor data regarding the received light. In some implementations, the electronic device may also include one or more electrical contacts that contact one or more body parts of the user. In such implementations, the health data may be further computed based on the an electrical measurement obtained using the electrical contacts.

In some implementations, the electronic device may utilize the camera to determine the user's body part is misaligned with the camera, the ambient light sensor, and the proximity sensor for purposes of detecting the information about the body part of the user. In such implementations, the electronic device may provide guidance to correct the misalignment.

In various embodiments, a mobile personal computing device may include a camera, an ambient light sensor, a proximity sensor, and a processing unit communicably coupled to the camera, the ambient light sensor, and the proximity sensor. The processing unit may be configured to: use at least one of camera and a proximity sensor to emit light into a body part of a user touching a surface of the mobile personal computing device; use at least one of the camera, an ambient light sensor, or the proximity sensor to receive at least part of the emitted light reflected by the body part of the user and generate sensor data; and computing health data of the user, utilizing the processing unit, using at least the sensor data regarding the received light.

In some embodiments, a method for using a mobile personal computing device to obtain health data may include: using at least one of camera and a proximity sensor to emit light into a body part of a user touching a surface of the device; using at least one of the camera, an ambient light sensor, or the proximity sensor to receive at least part of the emitted light reflected by the body part of the user and generate sensor data; and computing health data of the user, utilizing the processing unit, using at least the sensor data regarding the received light.

In one or more embodiments, a method for guiding use of a mobile personal computing device to obtain health data may include: detecting, utilizing a camera, a profile of a body part of a user contacting the camera; determining, using the profile, if the body part is misaligned with a combination of the camera, an ambient light sensor, and a proximity sensor for purposes of obtaining health data for the user; and providing guidance to correct the misalignment.

In various embodiments, a computer program product including a non-transitory storage medium may include a first set of instructions, stored in the non-transitory storage medium, executable by at least one processing unit to use at least one of a camera and a proximity sensor to emit light into a body part of a user touching a surface of a mobile personal computing device; a second set of instructions, stored in the non-transitory storage medium, executable by the least one processing unit to use at least one of the camera, an ambient light sensor, or the proximity sensor to receive at least part of the emitted light reflected by the body part of the user and generate sensor data; and a third set of instructions, stored in the non-transitory storage medium, executable by the least one processing unit to compute health data of the user using at least the sensor data regarding the received light.

It is to be understood that both the foregoing general description and the following detailed description are for purposes of example and explanation and do not necessarily limit the present disclosure. The accompanying drawings, which are incorporated in and constitute a part of the specification, illustrate subject matter of the disclosure. Together, the descriptions and the drawings serve to explain the principles of the disclosure.

DETAILED DESCRIPTION

Figure 1:
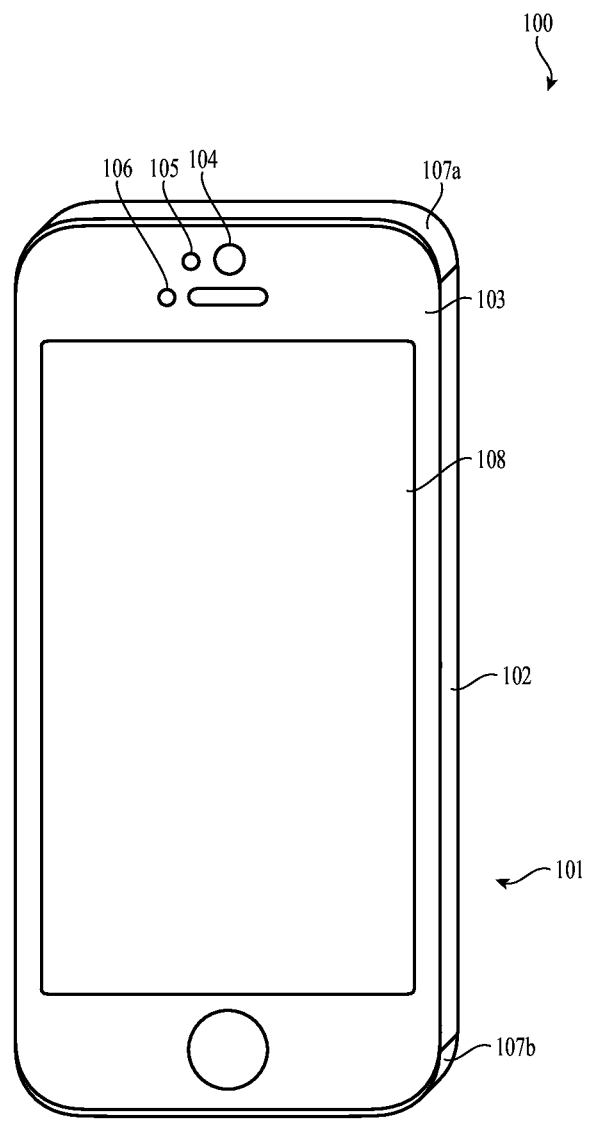
FIG. 1 is an isometric view an example system for obtaining health data utilizing an electronic device.

The description that follows includes sample systems, apparatuses, and methods that embody various elements of the present disclosure. However, it should be understood that the described disclosure may be practiced in a variety of forms in addition to those described herein.

The present disclosure details systems, apparatuses, and methods related to an electric device that computes health data. An electronic device (such as a smart phone, tablet computer, mobile computer, digital media player, wearable device, or other electronic device) may include a camera, an ambient light sensor, and a proximity sensor. The electronic device may use one or more of the camera and the proximity sensor to emit light into a body part of a user (such as a finger, and ear, and so on) touching a surface of the electronic device. The electronic device may use one or more of the camera, the ambient light sensor, and the proximity sensor to receive at least part of the emitted light reflected by the body part of the user. The electronic device may compute health data of the user based upon sensor data regarding the received light. In this way, the health data of the user may be detected utilizing an electronic device including a camera, ambient light sensor, and proximity sensor without making the user obtain access to a dedicated fitness and/or wellness device.

In various implementations, the camera, ambient light sensor, and proximity sensor may be positioned such that they are all at least partially covered (and/or contacted) by the user's body part at the same time, such as when the health data is computed. In one or more implementations, the electronic device may also include electrical contacts. The health data of the user may also be computed using an electrical measurement obtained using from the electrical contacts. In some examples of such implementations, the electrical contacts may be positioned to contact the body part of the user and an additional body part such that electrical measurement represents the electrical properties of organs or portions of the body located between the two contacting body parts. In some embodiments, the two body parts are the user's left and right hands and the electrical measurement corresponds to an electrical property that is measured across the user's chest.

In some implementations, the electronic device may utilize the camera to determine the user's body part is misaligned with the camera, the ambient light sensor, and the proximity sensor for purposes of detecting the information about the body part of the user. In such implementations, the electronic device may provide guidance (such as visual, audio, haptic, and/or other guidance) to correct the misalignment. The information from the camera may be utilized to detect this misalignment even in implementations where the camera is configured with a focal distance greater than a distance between the camera and the user's body part when the user's body part is touching the surface of the electronic device.

In various implementations, the proximity sensor may be a multiple light wavelength sensor (such as a sensor that utilizes infrared and visible light, infrared and red light, and so on). In some implementations, the ambient light sensor may be a silicon ambient light sensor, an indium gallium arsenide ambient light sensor, and/or other kind of ambient light sensor. In various implementations, the camera may be both an infrared and visible light camera.

The health data may include one or more of a variety of different wellness, fitness, and/or other parameters relating to the health of a user. For example, in various implementations the health data may include: a blood pressure index, a blood hydration, a body fat content, an oxygen saturation, a pulse rate, a perfusion index, an electrocardiogram, a photoplethysmogram, and/or any other such health data. In some implementations, the electronic device may provide the computed health data to the user.

FIG. 1 is an isometric view an example system 100 for obtaining health data utilizing an electronic device. As illustrated, the system may include an electronic device 101. The electronic device is shown as a smart phone. However, it is understood that this is an example. In various implementations, the electronic device may be any kind of electronic device such as any kind of mobile personal computing device (such as a smart phone, tablet computer, a mobile computer, a digital media player, a cellular telephone, a laptop computer, a wearable device, and so on), a desktop computer, a display, and/or any other electronic device.

Figure 2:
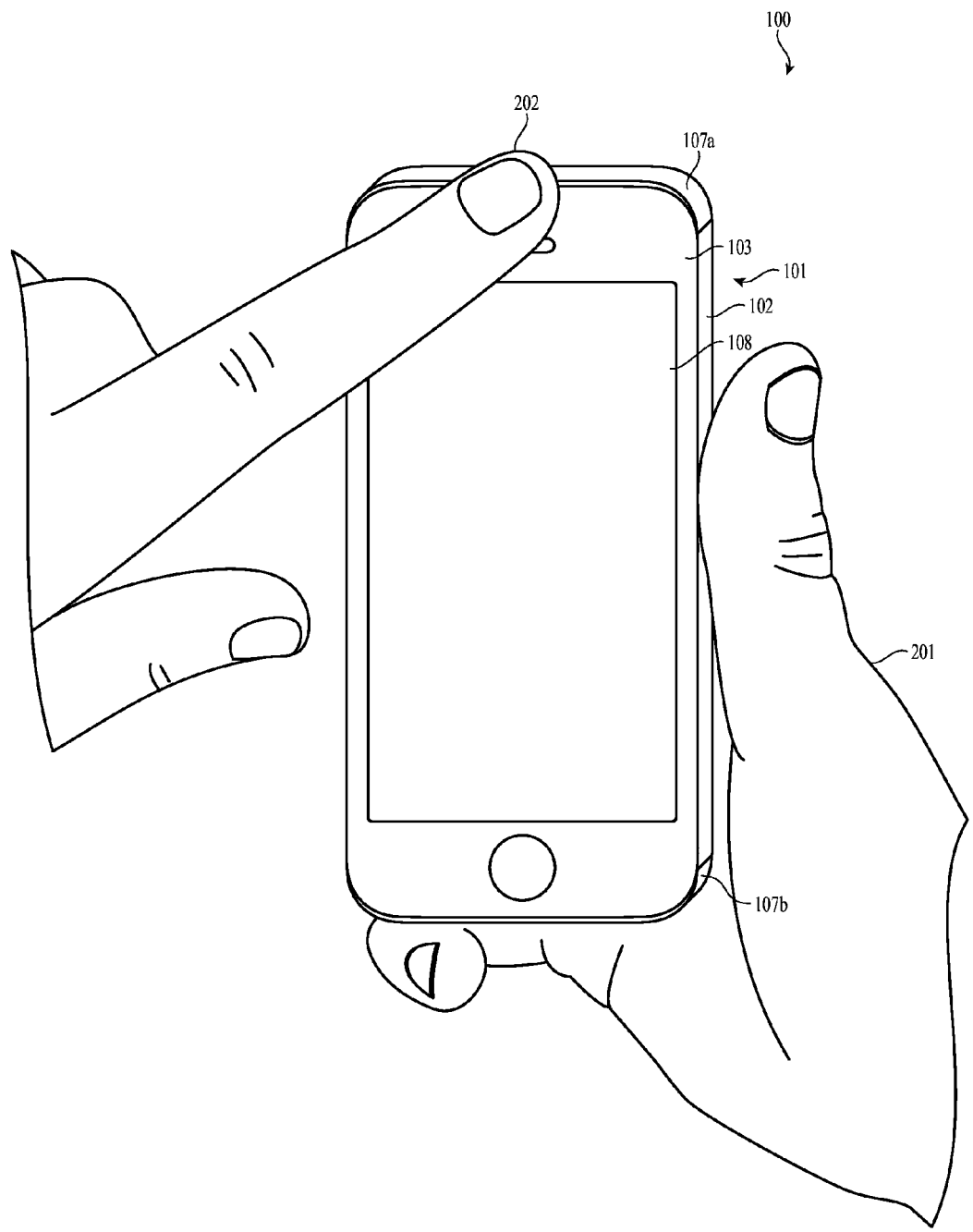
FIG. 2 illustrates the view of FIG. 1 while the example system is being utilized to obtain health data.

As also illustrated, the electronic device 101 may include a housing 102 with a surface 103 where a camera 104, an ambient light sensor 105, and a proximity sensor 106 are positioned. As illustrated in FIG. 2, the camera, ambient light sensor, and proximity sensor may be positioned such that they are partially or entirely covered (and/or contacted) by the body part 202 of a user (illustrated as a finger though such a body part may be an ear, a palm, and/or other body part of the user) at the same time. At such a time, the electronic device may compute health data for the user.

Traditionally, a camera may be capture images using a visible light imaging sensor and a lens focused at a focal distance away from the lens, an ambient light sensor may use a broad range photodiode or similar non-imaging light detector to determine ambient light conditions, and a proximity sensor may use a limited range light source (such as an infrared light emitting diode or "LED") to emit limited range light and a limited range non-imaging light detector to detect if the emitted limited range light is reflected by one or more object to determine whether or not such an object is proximate to the proximity sensor. However, the electronic device 101 may camera 104, the ambient light sensor 105, and the proximity sensor 106 in non-traditional ways to detect information about the body part 202.

The electronic device 101 may use one or more of the camera 104 and the proximity sensor 106 to emit light into a body part of a user 202 touching a surface 103 of the electronic device. The electronic device may use one or more of the camera, the ambient light sensor 105, and the proximity sensor to receive at least part of the emitted light reflected by the body part of the user. The electronic device may compute health data of the user based upon sensor (such as the camera, the ambient light sensor, and/or the proximity sensor) data regarding the received light.

For example, one or more of the camera 104, the ambient light sensor 105, and the proximity sensor 106 may receive light reflected off of the body part 202 of the user. Such light may originate from one or more of the camera (in implementations where the camera includes a light source such as a LED used as a flash), the ambient light sensor (which may be a non-imaging photodiode in some implementations), the proximity sensor (such as in implementations where the proximity sensor is a non-imaging photodiode and one or more LEDs that determine proximity by measuring the time between transmission of light by the LED and receipt of the light by the non-imaging photodiode after reflection off of an object such as the body part 202 of the user), and/or other light source. The electronic device 101 may analyze sensor data regarding the received light and compute information such as the light absorption of the body part. Various health data for the user may be computed from the computed light absorption of the body part.

By way of illustration, sensor data regarding the received light may be used to estimate changes in the volume of the body part 202 of the user. In general, as light passes through the user's skin and into the underlying tissue, some light is reflected, some light is scattered, and some light is absorbed, depending on what the light encounters. In some instances, blood may absorb light more than surrounding tissue, so less reflected light may be sensed when more blood is present. the user's blood volume generally increases and decreases with each heartbeat. Thus, analysis of sensor data regarding the reflected light may reflect changes in blood volume and thus allow health data such as oxygen saturation, pulse rate, perfusion index, and such to be computed.

By way of another example, one or more images of the body part 202 of the user captured by the camera 104 may be analyze to compute various health data for the user. In some implementations, the camera may be an infrared camera and/or a combined visible light and infrared camera. In such implementations, infrared data in the image may be analyzed to compute temperature of the body part, changing blood flow in the body part, and so on. In various implementations, the ambient light sensor and/or proximity sensor may be utilized to obtain such infrared data regarding the body part.

In various implementations, various information may be obtained regarding the body part 202 utilizing data from the camera 104, the ambient light sensor 105, and the proximity sensor 106. Such information may be utilized in a variety of different ways. For example, in some implementations each of the camera, the ambient light sensor, and the proximity sensor may capture sensor data regarding light absorption of the body part 202. However, the light absorption represented by the light received by each may be different based on the particular sensor strengths and/or weaknesses of the respective device. In such an implementation, the sensor data related to light absorption from each may be compared to the others and/or combined in order to obtain a more accurate, single light absorption measurement.

By way of another example, in some implementations sensor data from one or more of the camera 104, the ambient light sensor 105, and the proximity sensor 106 may be used to adjust information from one or more others of the camera, the ambient light sensor, and the proximity sensor. For example, in various implementations the proximity sensor may be utilized to obtain sensor data related to light absorption of the body part 202 and the camera may be utilized to determine the specific area of the body part the information relates to. Light absorption may be interpreted differently in computing health data for different areas of the body part (such as where the area of the body part is hairless versus containing hair, where the area is a highly callused area as opposed to a non-callused area, and so on). As such, the sensor data from the camera regarding the specific area of the body part being analyzed may be utilized to adjust the sensor data related to light absorption obtained from the proximity sensor to account for the specific characteristics of the area of the body part that may influence interpretation of light absorption for computing health data for the user.

As also illustrated in FIGS. 1 and 2, the electronic device 101 may also include electrical contacts such as electrical contacts 107a and 107b disposed on an exterior surface of the electronic device. In various implementations, the electronic device 101 may compute health data of the user based upon sensor data obtained from the camera 104, the ambient light sensor 105, and the proximity sensor 106 as well as an electrical measurement obtained using the electrical contacts.

As illustrated in FIG. 2, the electrical contacts 107a and 107b may be positioned to contact the body part 202 of the user (such as during the time when the information is being detected) and/or an additional body part 201 of the user. For example, as shown a finger of the user may contact a top electrical contact 107a while a palm of the user contacts a bottom electrical contact 107b. However, it is understood that this is an example and the electrical contacts may be configured to contact other body parts of the user (such as an ear, a cheek, and so on) without departing from the scope of the present disclosure.

In some implementations, the electrical contacts 107a and 107b may be positioned to contact the body part 202 of the user and an additional body part of the user such that electrical measurement obtained using the electrical contacts corresponds to an electrical characteristic across the user's chest. For example, as shown a finger of the user's left hand may contact a top electrical contact 107a while a right palm of the user (connected to each other through the user's chest) contacts a bottom electrical contact 107b. Positioning the electrical contacts to contact user body parts such that the electrical measurement obtained using the electrical contacts corresponds to an electrical property across the user's chest. Such a measurement may enable information related to health data (such as an electrocardiogram) to be obtained that might not otherwise be possible absent such positioning.

By way of illustration, electrical measurements may be taken via the electrical contacts 107a and 107b (which may respectively be configured as positive and negative terminals) that may be used to detect electrical activity of the user's body. Such electrical measurements may be used (in some cases along with analysis of the received light) to measure heart function, compute an electrocardiogram, compute a galvanic skin response that may be indicative of emotional state and/or other physiological condition, and/or compute other health data such as body fat, or blood pressure.

Although FIG. 1 illustrates a specific configuration including the camera 104, the ambient light sensor 105, the proximity sensor 106, and the electrical contacts 107a and 107b, it is understood that this in an example. In various implementations other configurations are possible and contemplated without departing from the scope of the present disclosure.

For example, the ambient light sensor 105 and the proximity sensor 106 are illustrated and described as separated sensors. However, in some implementations the ambient light sensor and the proximity sensor may be incorporated into a single, unified sensor that may detect both ambient light and proximity without departing from the scope of the present disclosure.

In some implementations, the proximity sensor 106 may operate utilizing a single wavelength of light, such as the infrared portion of the light spectrum. However, in other implementations the proximity sensor (and/or the camera 104 and/or the ambient light sensor 105) may be a multiple wavelength proximity sensor that operates utilizing multiple wavelengths of light.

For example, in various implementations the proximity sensor 106 may operate utilizing infrared and visible light (such as red light). In some embodiments of such an implementation, the proximity sensor may include an infrared LED for producing infrared light and a red LED for producing red light.

Sensor data obtained utilizing different wavelengths of light may be different based on the particular detection strengths and/or weaknesses of the respective wavelength. By utilizing multiple wavelengths, the information detected utilizing the various wavelengths may be combined and/or utilized to adjust each other in order to obtain greater accuracy.

For example, dark and light hairs may have different light absorption due to their different pigmentation regardless of their other physical characteristics. By averaging light absorption detected utilizing both infrared and red light, a more accurate light absorption that accounts for such color difference may be possible such that detecting light absorption of different colored hairs does not result in inaccurate measurements.

In some implementations, the ambient light sensor 105 may be a silicon ambient light sensor, such as a silicon non-imaging photodiode. In other implementations, the ambient light sensor 105 may be an indium gallium arsenide ambient light sensor, such as an indium gallium arsenide non-imaging photodiode. In various implementations, use of an indium gallium arsenide non-imaging photodiode may allow for detection of a larger spectrum of light than use of a silicon non-imaging photodiode. An indium gallium arsenide non-imaging photodiode may not be typically used as an ambient light sensor as such may be more expensive than a silicon non-imaging photodiode that may adequately be used to determine ambient light conditions by detecting a more limited spectrum of light.

In various implementations, a variety of different health data for the user may be computed based at least thereon. For example, in one or more implementations the health data may include one or more of a variety of different wellness, fitness, and/or other parameters relating to the health of a user such as: a blood pressure index, a blood hydration, a body fat content, an oxygen saturation, a pulse rate, a perfusion index, an electrocardiogram, a photoplethysmogram, and/or any other such health data.

Figure 7:
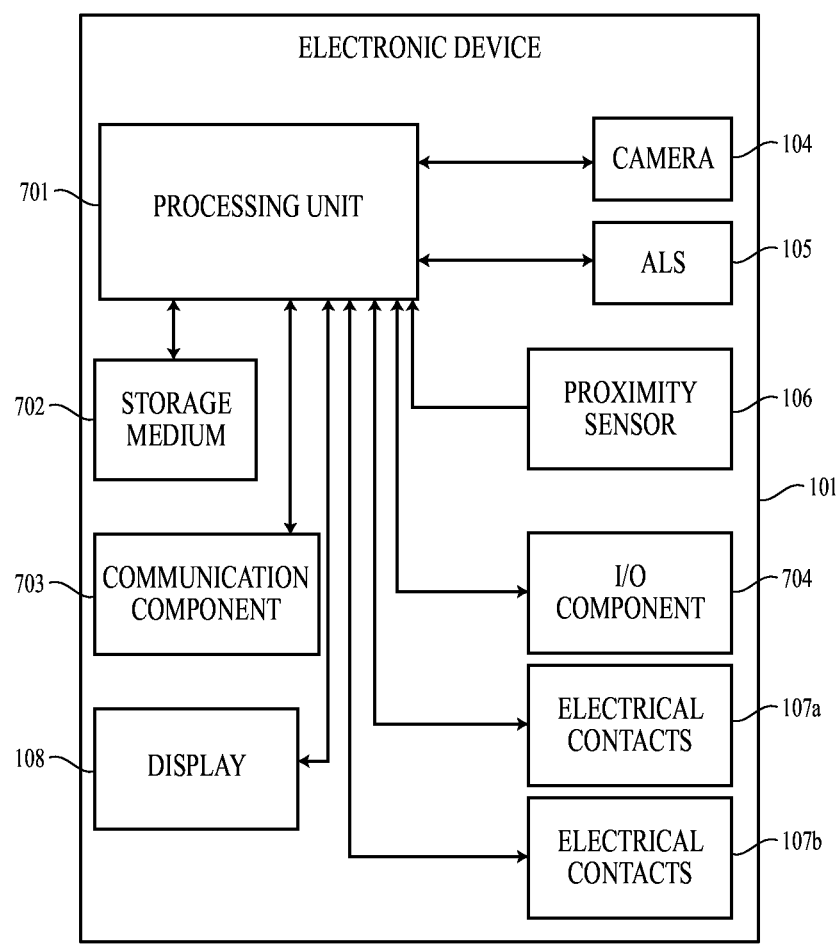
FIG. 7 is a block diagram illustrating functional relationships among components of the example system of FIG. 1.

FIG. 7 is a block diagram illustrating functional relationships among components of the example system 100 of FIG. 1. As shown, the electronic device 101 may include one or more processing units 701, one or more non-transitory storage media 702 (which may take the form of, but is not limited to, a magnetic storage medium; optical storage medium; magneto-optical storage medium; read only memory; random access memory; erasable programmable memory; flash memory; and so on), one or more communication components 703 (such as a Wi-Fi or other antenna that may be utilized to transmit computed health data for the user), one or more input/output components 704, a display 108 (which may be utilized to present computed health data for the user), the camera 104, the ambient light sensor 105, the proximity sensor 106, and/or the electrical contacts 107a and 107b. However, it is understood that this is an example. In various implementations, the electronic device 101 may omit one or more of these components and/or utilize one or more additional components not shown.

Returning to FIG. 2, in various implementations the electronic device 101 may provide guidance to the user for aligning the user's body part 202 with the camera 104, the ambient light sensor 105, the proximity sensor 106, and/or the electrical contacts 107a and 107b. Such correct alignment may aid in utilizing camera, the ambient light sensor, the proximity sensor, and/or the electrical contacts in detecting the information regarding the body part of the user. In some implementations, misalignment of the user's body part with the camera, the ambient light sensor, the proximity sensor, and/or the electrical contacts for purposes of obtaining the information may reduce the accuracy of the information and/or prevent detection of the information. As such, the guidance may aid in the detection of the information and/or the computing of the health data.

Figure 3:
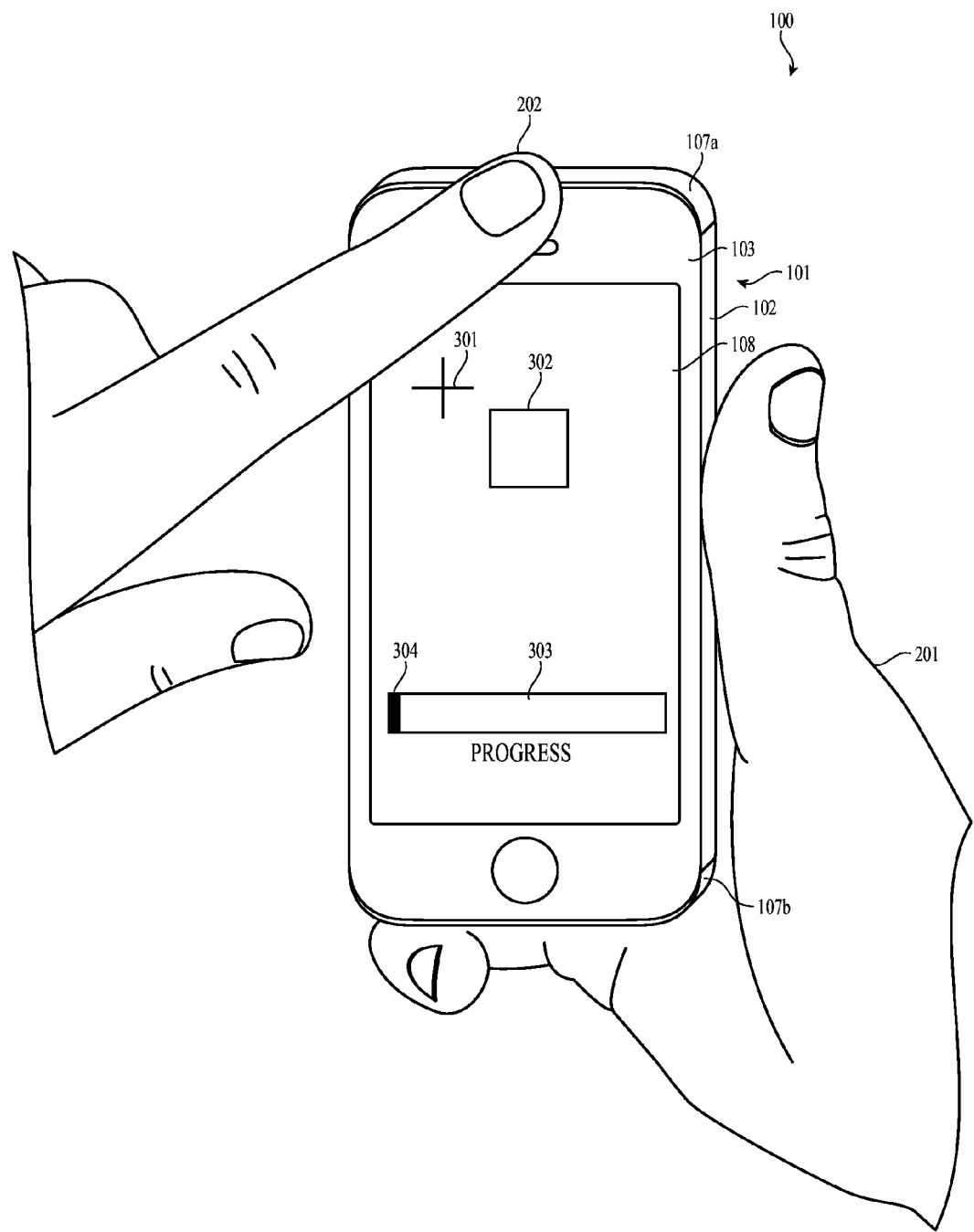
FIG. 3 illustrates the view of FIG. 2 while the example system is providing guidance to obtain health data.

For example, FIG. 3 illustrates the view of FIG. 2 while the example system 100 is providing guidance to obtain health data. As illustrated in this example, the electronic device 101 provides a current body part position indicator 301 and a goal position indicator 302. A user may compare the visual positions of the current body part position indicator and the goal position indicator to determine how to move the user's body part 202 into correct alignment. As shown, the user may move the user's body part down and to the right, aligning the current body part position indicator with the goal position indicator 302, to move the user's body part into correct alignment.

Further, the electronic device 101 may also provide a status indicator 303 that indicates a progress 304 of obtaining the information. In this way, the user may be alerted to how long the user should stay in position once the user aligns the user's body part so that the information may be detected.

In some implementations, the camera 104 may be utilized to detect the position of the user's body part for purposes of determining alignment/misalignment. The camera may be configured to detect this information even in implementations where the camera is configured with a focal distance greater than the distance from the camera to the user's body part 202 shown as less than full focused image quality may be adequate for determining alignment/misalignment. In other implementations, the ambient light sensor 105, the proximity sensor 106, the electrical contacts 107a and 107b, and/or other components may be utilized instead of and/or in addition to the camera for determining alignment/misalignment of the user's body part.

Although FIG. 3 illustrates the electronic device 101 providing guidance output graphically using a visual output component, it is understood that this is an example. In various implementations, such output may be provided in one or more of a variety of different ways. For example, audio guidance instructions may be provided utilizing an audio output component and/or vibration guidance instructions may be provided utilizing a haptic output component without departing from the scope of the present disclosure.

Figure 4:
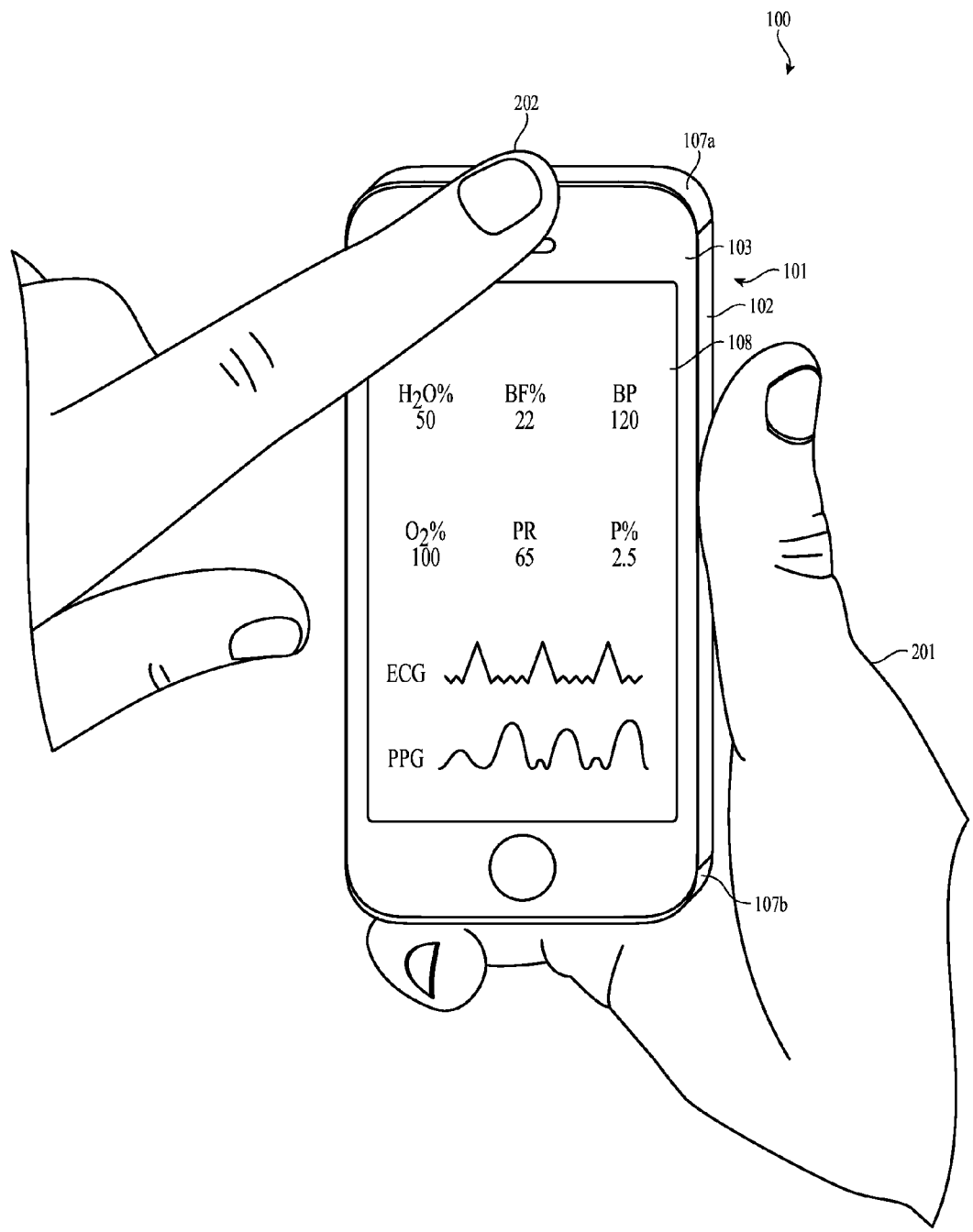
FIG. 4 illustrates the view of FIG. 2 while the example system is providing the obtained health data.

FIG. 4 illustrates the view of FIG. 2 while the example system 100 is providing the obtained health data. As illustrated, a variety of different health data may be presented. Although FIG. 4 illustrates the electronic device 101 providing the health data graphically using a visual output component, it is understood that this is an example. In various implementations, such health may be provided in one or more of a variety of different ways, such as audibly utilizing an audio output component without departing from the scope of the present disclosure. In other implementations, the health data may be communicated to another electronic device (such as a health data database maintained by a doctor and/or other medical or health provider) utilizing a communication component.

Figure 5:
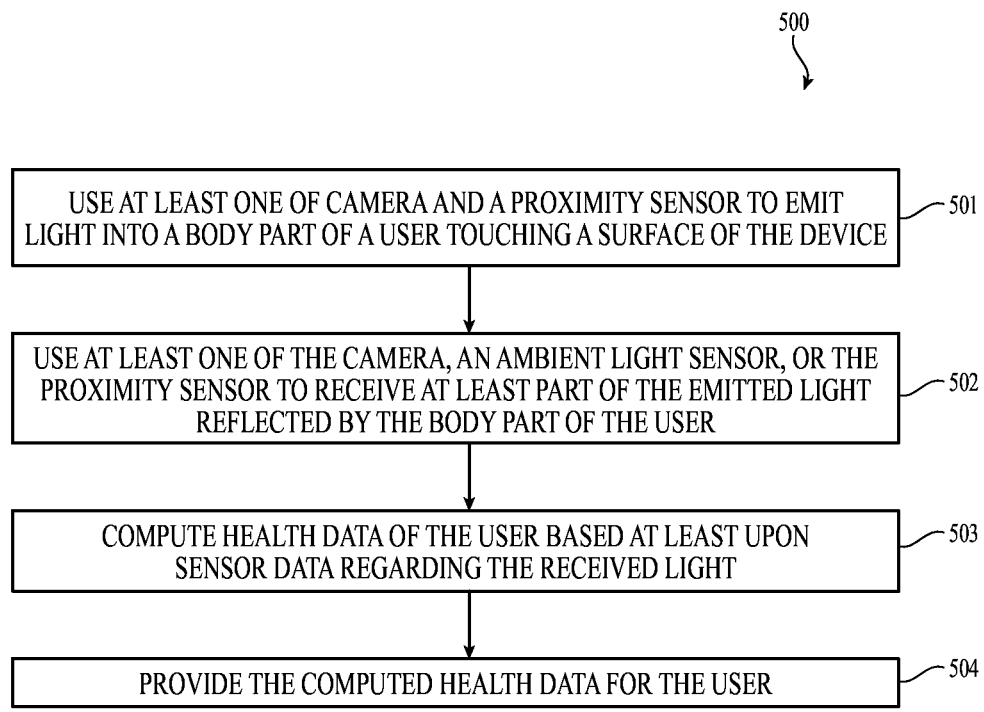
FIG. 5 is a flow chart illustrating an example method for using an electronic device to obtain health data. This method may be performed by the system of FIG. 1.

FIG. 5 is a flow chart illustrating an example method 500 for using an electronic device to obtain health data. This method may be performed by the system of FIG. 1.

The flow may begin at block 501 where at least one of camera and a proximity sensor may be used to emit light into a body part of a user touching a surface of the electronic device. The flow may proceed to block 502 where at least one of the camera, an ambient light sensor, or the proximity sensor may be used to receive at least part of the emitted light reflected by the body part of the user to produce sensor output and generate sensor data. The flow may then proceed to block 503 where health data of the user may be computed using at least the sensor data regarding the received light.

At block 504, the computed health data for the user may be provided. In some implementations, the computed health data for the user may be provided to the user. Such providing may be performed using one or more visual output components such as a display, audio output components such as a speaker, haptic output components, and so on.

In one example, the proximity sensor may be used to emit light into the user's body part, the ambient light sensor and the camera may be used to receive at least part of the emitted light reflected by the user's body part, and electrical contacts may be used to obtain electrical measurements from the skin of the user's body part. In such an example, a blood pressure index, a body fat content, and an electrocardiogram may be computed using data from the ambient light sensor, the camera, and the electrical contacts.

In another example, the proximity sensor may be a multiple light wavelength proximity sensor that utilizes infrared and visible light and the ambient light sensor may be a indium gallium arsenide ambient light sensor. The proximity sensor may be used to emit light into the user's body part, the ambient light sensor and the camera may be used to receive at least part of the emitted light reflected by the user's body part, and electrical contacts may be used to obtain electrical measurements from the skin of the user's body part. In such an example, a blood hydration may be computed using data from the ambient light sensor, the camera, and the electrical contacts.

In yet another example, the proximity sensor may be used to emit light into the user's body part and the ambient light sensor and the camera receive at least part of the emitted light reflected by the user's body part. In such an example, an oxygen saturation, a pulse rate, a perfusion index and a photoplethysmogram may be computed using data from the ambient light sensor and the camera.

Although the example method 500 is illustrated and described above as including particular operations performed in a particular order, it is understood that this is an example. In various implementations, various orders of the same, similar, and/or different operations may be performed without departing from the scope of the present disclosure.

For example, block 503 is illustrated and described as providing the computed health data for the user. However, in various implementations this operation may be omitted. In some examples of such an implementation, the computed health data for the user may be stored for later use as opposed to being provided to the user.

Figure 6:
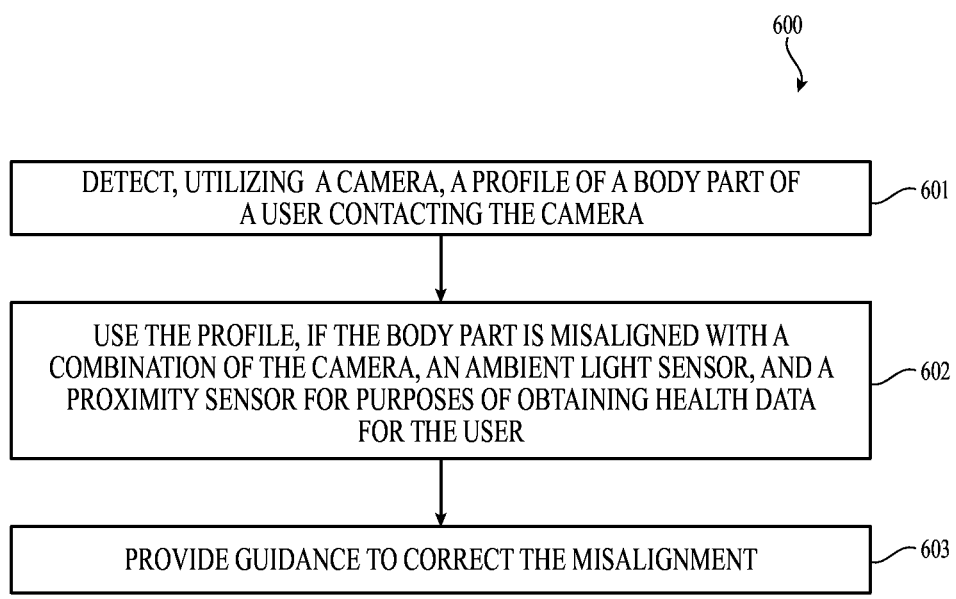
FIG. 6 is a flow chart illustrating an example method for guiding use of an electronic device to obtain health data. This method may be performed by the system of FIG. 1.

FIG. 6 is a flow chart illustrating an example method 600 for guiding use of an electronic device to obtain health data. This method may be performed by the system of FIG. 1.

The flow may begin at block 601 where at least a profile of a body part of a user (such as the outline, location, or orientation) contacting a camera may be detected using a camera. The flow may proceed to block 602 where it is determined based on the detection that the user's body part is misaligned with a combination of the camera, an ambient light sensor, and a proximity sensor for purposes of obtaining health data for the user.

Detection of the user's body part may include comparing the profile to data representing a correct alignment. For example, an image of the profile of the user's body part may be captured and compared to a sample image representing what the image of the profile of the user's body part should look like if the user's body part is correctly aligned. A mismatch may indicate that the user's body part is misaligned.

At block 603, guidance to correct the misalignment may be provided. In the example discussed above where a mismatch between the image of the profile of the user's body part and the sample image indicated that the user's body part was misaligned, the differences between the two images may be utilized to determine guidance to provide. By way of illustration, if the image of the profile of the user's body part has the user's body part further to the left than the sample image then it may be determined that the user should more the user's body part to the right. Such guidance may be provided using one or more visual output components such as a display, audio output components such as a speaker, haptic output components such as a vibrator, and so on.

For example, a user may place his finger on the camera. An image may be taken of the profile of the user's finger and compared to a sample image of what the profile of the user's finger should look like if correctly aligned with a combination of the camera, an ambient light sensor, and a proximity sensor for purposes of obtaining health data for the user. Comparison of the two images may indicate that the two images do not match and the user's finger is not correctly aligned. In this example, the image of the profile of the user's finger may be further up and to the right of the sample image. As such, a correct placement indicator and a current placement indicator may be displayed to the user where the current placement indicator is displayed further up and to the right of the correct placement indicator. In this way, the user can see that to correctly align the user's finger the user should move the user's finger down and to the left.

To continue with this example, the user may move the user's finger based on the provided guidance. A new image may be taken of the current profile of the user's finger and compared to the sample image. Comparison of the two images may indicate that the two images, though closer, still do not match and the user's finger is not still correctly aligned. In this example, the image of the profile of the user's finger may be less but still further up and to the right of the sample image. As such, the current placement indicator may be displayed moved closer but still further up and to the right of the correct placement indicator. In this way, the user can see that to correctly align the user's finger the user should move the user's finger still further down and to the left.

The process in this example may be repeated until comparison of an image of profile of the user's finger matches the sample image. The current placement indicator may then be displayed over the correct placement indicator to indicate to the user that the user's finger is correctly aligned and to not move further until health data is obtained.

Although the example method 600 is illustrated and described above as including particular operations performed in a particular order, it is understood that this is an example. In various implementations, various orders of the same, similar, and/or different operations may be performed without departing from the scope of the present disclosure.

For example, though blocks 601-603 are described as a series of linear operations that are performed a single time, it is understood that this is an example. In various implementations, one or more of blocks 601-603 may be repeated until the user's body part is no longer misaligned without departing from the scope of the present disclosure.

As discussed above and illustrated in the accompanying figures, the present disclosure details systems, apparatuses, and methods related to an electric device that computes health data. An electronic device (such as a smart phone, tablet computer, mobile computer, digital media player, wearable device, or other electronic device) may include a camera, an ambient light sensor, and a proximity sensor. The electronic device use one or more of the camera and the proximity sensor to emit light into a body part of a user (such as a finger, and ear, and so on) touching a surface of the electronic device. The electronic device may use one or more of the camera, the ambient light sensor, and the proximity sensor to receive at least part of the emitted light reflected by the body part of the user. The electronic device may compute health data of the user based upon sensor data regarding the received light. In this way, the health data of the user may be detected utilizing an electronic device including a camera, ambient light sensor, and proximity sensor without making the user obtain access to a dedicated fitness and/or wellness device.

In the present disclosure, the methods disclosed may be implemented as sets of instructions or software readable by a device. Further, it is understood that the specific order or hierarchy of steps in the methods disclosed are examples of sample approaches. In other embodiments, the specific order or hierarchy of steps in the method can be rearranged while remaining within the disclosed subject matter. The accompanying method claims present elements of the various steps in a sample order, and are not necessarily meant to be limited to the specific order or hierarchy presented.

Techniques detailed in the described disclosure may be provided as a computer program product, or software, that may include a non-transitory machine-readable medium having stored thereon instructions, which may be used to program a computer system (or other electronic devices) to perform a process according to the present disclosure. A non-transitory machine-readable medium includes any mechanism for storing information in a form (e.g., software, processing application) readable by a machine (e.g., a computer). The non-transitory machine-readable medium may take the form of, but is not limited to, a magnetic storage medium (e.g., floppy diskette, video cassette, and so on); optical storage medium (e.g., CD-ROM); magneto-optical storage medium; read only memory (ROM); random access memory (RAM); erasable programmable memory (e.g., EPROM and EEPROM); flash memory; and so on.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context or particular embodiments. Functionality may be separated or combined in blocks differently in various embodiments of the disclosure or described with different terminology. These and other variations, modifications, additions, and improvements may fall within the scope of the disclosure as defined in the claims that follow.

I claim:

1. A mobile personal computing device, comprising:
   a camera;
   an ambient light sensor;
   a proximity sensor; and
   a processing unit communicably coupled to the camera, the ambient light sensor, and the proximity sensor;
   wherein the processing unit is configured to:
      use the camera and the proximity sensor to emit light into a body part of a user touching a surface of the mobile personal computing device;
      use at least one of the camera, an ambient light sensor, or the proximity sensor to receive at least part of the emitted light reflected by the body part of the user and generate sensor data; and
      compute health data of the user, utilizing the processing unit, using at least the sensor data regarding the received light.

2. The mobile personal computing device of claim 1, wherein the camera, the ambient light sensor, and the proximity sensor are positioned to be at least partially covered by the body part of the user at a same time.

3. The mobile personal computing device of claim 1, wherein the proximity sensor is configured to detect multiple wavelengths of light.

4. The mobile personal computing device of claim 3, wherein multiple light wavelength proximity sensor is configured to emit and receive infrared and visible light.

5. The mobile personal computing device of claim 3, wherein multiple light wavelength proximity sensor is configured to emit and receive infrared and red light.

6. The mobile personal computing device of claim 1, wherein the ambient light sensor is a at least one of a silicon ambient light sensor or an indium gallium arsenide ambient light sensor.

7. The mobile personal computing device of claim 1, wherein the camera is configured to detect infrared light.

8. The mobile personal computing device of claim 1, wherein the device is configured to compute the health-related information when the body part of the user is positioned at least partially over the camera, the ambient light sensor, and the proximity sensor.

9. The mobile personal computing device of claim 1, wherein the processing unit utilizes the camera to determine when the body part of the user is misaligned with the camera, the ambient light sensor, and the proximity sensor for purposes of detecting the information about the body part of the user.

10. The mobile personal computing device of claim 9, wherein the processing unit provides an output that can be used as guidance to correct a misalignment.

11. The mobile personal computing device of claim 10, wherein the processing unit is configure to provide the output to at least one visual output component, audio output component, or haptic output component.

12. The mobile personal computing device of claim 1, wherein the camera is configured with a focal distance greater than a distance between the camera and the body part of the user when the body part is touching the surface of the mobile personal computing device.

13. The mobile personal computing device of claim 1, further comprising
   electrical contacts disposed on an exterior surface of the device, wherein the processing unit is further configured to compute additional health-related information regarding the user based on an electrical measurement obtained using the electrical contacts.

14. The mobile personal computing device of claim 13, wherein the electrical contacts are positioned to contact the body part of the user and an additional body part of the user.

15. The mobile personal computing device of claim 14, wherein the electrical measurement obtained using the electrical contacts corresponds to an electrical property across the user's chest.

16. The mobile personal computing device of claim 13, wherein the processing unit is further configured to:
   use at least the proximity sensor to emit the light;
   use the ambient light sensor and the camera to receive the reflected light; and
   compute a blood pressure index, a body fat content, and an electrocardiogram using data from the ambient light sensor, the camera, and the electrical contacts.

17. The mobile personal computing device of claim 13, wherein the proximity sensor is a multiple light wavelength proximity sensor that utilizes infrared and visible light, the ambient light sensor is a indium gallium arsenide ambient light sensor, and the processing unit is further configured to:
   use at least the proximity sensor to emit the light;
   use the ambient light sensor and the camera receive the reflected light; and
   compute a blood hydration using data from the ambient light sensor, the camera, and the electrical contacts.

18. The mobile personal computing device of claim 1, wherein the processing unit is further configured to:
   use at least the ambient light sensor and the camera receive the reflected light; and
   compute an oxygen saturation, a pulse rate, a perfusion index, or a photoplethysmogram using data from the ambient light sensor and the camera.

19. The mobile personal computing device of claim 1, wherein the processing unit is configured to use data from the camera indicating characteristics of the body part that influence light absorption to adjust the sensor data regarding the received light as part of computing the health data.

20. A method for using a mobile personal computing device to obtain health data, comprising:
   using a camera and a proximity sensor to emit light into a body part of a user touching a surface of the mobile personal computing device;
   using at least two of the camera, an ambient light sensor, or the proximity sensor to receive at least part of the emitted light reflected by the body part of the user and generate sensor data; and
   computing health data of the user, utilizing the processing unit, using at least the sensor data regarding the received light.

21. A computer program product including a non-transitory storage medium, comprising:
   a first set of instructions, stored in the non-transitory storage medium, executable by at least one processing unit to use a camera and a proximity sensor to emit light into a body part of a user touching a surface of a mobile personal computing device;
   a second set of instructions, stored in the non-transitory storage medium, executable by the least one processing unit to use the camera and an ambient light sensor to receive at least part of the emitted light reflected by the body part of the user and generate sensor data; and
   a third set of instructions, stored in the non-transitory storage medium, executable by the least one processing unit to compute health data of the user using at least the sensor data regarding the received light.

* * * * *